United States Patent
James, IV et al.

(10) Patent No.: US 6,522,806 B1
(45) Date of Patent: Feb. 18, 2003

(54) OPTICAL FIBER INCLUDING A DIFFUSER PORTION AND CONTINUOUS SLEEVE FOR THE TRANSMISSION OF LIGHT

(75) Inventors: Benjamin F. James, IV, Mason, OH (US); Gregory Bakos, Mason, OH (US); Donald E. Nitsche, Alden, NY (US)

(73) Assignee: Ethicon Endo-Surgury, Inc., Cinncinati, OH (US)

(*) Notice: Subject to any disclaimer, the term of this patent is extended or adjusted under 35 U.S.C. 154(b) by 14 days.

(21) Appl. No.: 09/785,571

(22) Filed: Feb. 16, 2001

(51) Int. Cl.[7] ............................. G02B 6/26; G02B 6/42
(52) U.S. Cl. ..................... 385/31; 385/902; 385/15; 606/15; 606/16; 264/1.24; 264/1.25
(58) Field of Search ................... 385/31, 139, 38, 385/402, 134, 76; 606/15, 13, 14, 16, 17; 604/20, 21; 264/1.1, 1.24, 1.25

(56) References Cited

U.S. PATENT DOCUMENTS

| | | | |
|---|---|---|---|
| 4,660,925 A | | 4/1987 | McCaughan, Jr. |
| 4,693,556 A | | 9/1987 | McCaughan, Jr. |
| 4,986,628 A | | 1/1991 | Lozhenko et al. |
| 5,074,632 A | | 12/1991 | Potter |
| 5,188,632 A | * | 2/1993 | Goldenberg ............... 385/142 |
| 5,196,005 A | | 3/1993 | Doiron et al. |
| 5,207,669 A | * | 5/1993 | Baker et al. ................ 606/15 |
| 5,269,777 A | | 12/1993 | Doiron et al. |
| 5,401,270 A | * | 3/1995 | Muller et al. ................ 606/13 |
| 5,534,000 A | * | 7/1996 | Bruce ......................... 606/11 |
| 5,695,583 A | * | 12/1997 | van den Bergh et al. ... 156/153 |
| 5,754,717 A | | 5/1998 | Esch |
| 5,802,229 A | | 9/1998 | Evans et al. |
| 5,814,041 A | | 9/1998 | Anderson et al. |
| 6,270,492 B1 | * | 8/2001 | Sinofsky ..................... 606/13 |
| 6,315,775 B1 | * | 11/2001 | Thielen et al. .............. 362/558 |
| 6,361,530 B1 | * | 3/2002 | Mersch ...................... 264/1.24 |

FOREIGN PATENT DOCUMENTS

EP 0673627 A 9/1995

OTHER PUBLICATIONS

J. C. Mizeret et al., "Cylindrical Fiberoptic Light Idffuser for Medical Applications", Lasers in Surgery and Medicine, Wiley–Liss, New York, vol. 19, No. 2 pp. 159–167, 1996.

* cited by examiner

*Primary Examiner*—Hemang Sanghavi
*Assistant Examiner*—Scott A Knauss
(74) *Attorney, Agent, or Firm*—Gerry S. Gressel

(57) ABSTRACT

A novel optical fiber, and a method for its production, having a diffuser portion and continuous unitarily-constructed outer sleeve, which is adapted for the transmission of light to a treatment locale. More particularly, a medical instrument has an optical fiber including a diffuser portion at a distal end wherein an alignment sleeve for the optical fiber extends uninterruptedly in a single piece from a connector for a laser light source to at least the distal end of the core of the optical fiber.

12 Claims, 2 Drawing Sheets

OPTICAL FIBER INCLUDING A DIFFUSER PORTION AND CONTINUOUS SLEEVE FOR THE TRANSMISSION OF LIGHT

BACKGROUND OF THE INVENTION

1. Field of the Invention

The present invention relates, in general, to a novel optical fiber having a diffuser portion and continuous unitarily-constructed outer sleeve, which is adapted for the transmission of light to a treatment locale. More particularly, the invention relates to a medical instrument with an optical fiber including a diffuser portion at a distal end wherein an alignment sleeve for the optical fiber extends uninterruptedly in a single piece from a connector for a laser light source to at least the distal end of the core of the optical fiber.

Currently, surgeons frequently employ medical instruments which incorporate laser technology in the treatment of benign prostatic hyperplasia, or as commonly referred to as BPH. BPH is a condition of an enlarged prostate gland, in which the gland having BPH typically increases in size to between about two to four times from normal. The lasers which are employed by the surgeons to treat this condition must have durable optical fibers that distribute light radially in a predictable and controlled manner, and must also be capable of bending without breaking, whereby small-sized or slender optical fibers offer an additional advantage to the surgeon.

An optical fiber which is adapted to be employed for this purpose typically contains a glass core surrounded by cladding, a buffer layer, and an outer alignment sleeve. The cladding protects the inherently weaker glass core by imparting a mechanical support to the core. The cladding also ordinarily possesses an index of refraction which is lower than that of the core in order to block light transmitted through the optical fiber from emerging radially from the core. Although optical fibers which are utilizable for such surgical procedures and treatments are widely known and successfully employed, the present invention is designed to provide further significant improvements and advantages over the state-of-the art.

2. Discussion of the Prior Art

An optical fiber with a diffuser portion for diffusing light emitted at an end thereof is disclosed in Esch U.S. Pat. No. 5,754,717 as shown in FIG. 1 of this application, which patent is commonly assigned to the present assignee, and the disclosure of which is incorporated herein by reference. There is illustrated an optical fiber leading end 10 having a diffuser portion 12 comprised of the stripped core of a typical optical laser, an optical coupling layer, and an outer or alignment sleeve 14. The optical coupling layer, replacing a part of the cladding and the buffer layer of the optical fiber, has an index of refraction exceeding that of the core so as to draw the light out of the core using well-known physical principles. The alignment sleeve is abraded, or roughened, in order to conduct light from the optical coupling layer to the exterior, while heat staking or ultrasonic welding is used to apply or attach the portion of 14a of the outer sleeve 14 covering the diffuser tip to a further separate portion 14b of the sleeve located towards the end of the optical fiber.

In essence, the method of forming the diffusion portion of the optical fiber illustrated in FIG. 1 representing the Esch patent, necessitates the presence of a weld joint 16 near the distal end of the remaining cladding. Producers of optical fibers with diffuser portions intended for this or similar surgical purposes are required to ensure an adequate mechanical strength of the fiber for the intended application, and in which the weld joint can result in a stress concentration reducing the strength of the optical fiber. It is also possible that silicone or adhesive from the optical coupling layer may contaminate the area of the sleeve junction during assembly, thereby weakening the weld joint. While the weld joint is deemed to be of adequate strength for most surgical applications, designers would like to use smaller-sized optical fibers. As the diameter of optical fibers become smaller, the degradation in strength of the optical fiber caused by the presence of the weld joint becomes more pronounced and resultingly important. The smaller diffusers can readily break or become detached at the weld joint; whereas the weld seam at the weld joint can catch on instruments and interfere with the medical procedure, thereby creating a nuisance, if not an operating danger for the surgeon.

Other publications which disclose various constructions and types of optical fiber arguments which may be applicable to surgical procedures and treatments employing laser illumination are widely known in the technology.

Anderson et al. U.S. Pat. No. 5,814,041 pertains to an optical radiator and laser fiber in which the distal or leading end sleeve portion of the optical fiber is attached to a second sleeve portion so as to form a weld or contact seam therebetween.

Evans et al. U.S. Pat. No. 5,802,229 discloses a fiber optic radiation system which, similar to Esch, does not provide for a continuous, unitarily constructed outer sleeve for the optic fiber.

Bruce U.S. Pat. No. 5,534,000 discloses a laser fiber apparatus wherein the leading or ablation end of an optic fiber is provided with a relatively short outer tube element so as form an essentially non-continuous sleeve surface providing a seam-like joint or step.

Similarly, Doiron et al. U.S. Pat. Nos. 5,269,777 and 5,196,005; and McCaughan, Jr. U.S. Pat. Nos. 4,693,556 and 4,660,925, disclose various types of optical fibers with light diffusers or similar structures; however, none of which evidence the continuous single-piece outer sleeve of seamless length as provided for by the present invention, nor the method of forming thereof

SUMMARY OF THE INVENTION

Accordingly, the design of an optical fiber with a diffuser portion including an outer sleeve wherein the weld joint is eliminated is highly advantageous in constructing the sleeve of the optical fiber extending as one continuous, uninterrupted or unitary piece from the connector for a light source to the distal end of the core.

Pursuant to the invention, a medical instrument comprises a source for a laser light wherein an optical fiber with a diffuser portion at its distal end has the outer sleeve of the optical fiber constituted of a continuous unitarily-constructed tube extending from the connector for the laser-light source to at least the distal end of the core in the optical fiber. The sleeve of the optical fiber also contacts and supports the optical fiber at the leading or light emitting distal end thereof Accordingly, it is an object of the present invention to provide a method of producing an optical laser fiber arrangement in which the outer tubular sleeve encompassing the fiber core is of a continuous, unitarily constructed and seamless tubular structure.

Another object of the present invention is to provide a medical instrument incorporating an optical laser fiber produced in accordance with the inventive method for forming the optical fiber portion of the instrument.

BRIEF DESCRIPTION OF THE DRAWINGS

Reference may now be made to the following detailed description of preferred embodiment of the invention, taken in conjunction with the accompanying drawings; in which.

DETAILED DESCRIPTION OF PREFERRED EMBODIMENTS

Referring in detail to the drawings, for purposes of this description, "proximal" refers to a section on the inventive optical fiber 28 closer to a source of light energy 22, and "distal" refers to a section on the optical fiber which is further away from the source of light energy 22.

Figure 1:
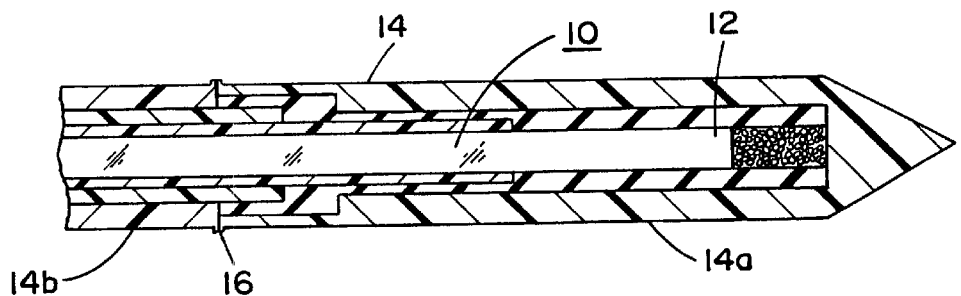
FIG. 1 illustrates a longitudinal sectional view of an optical fiber utilizing the diffuser portion as shown in the Esch U.S. Pat. No. 5,754,717, representative of the prior art.
Figure 2:
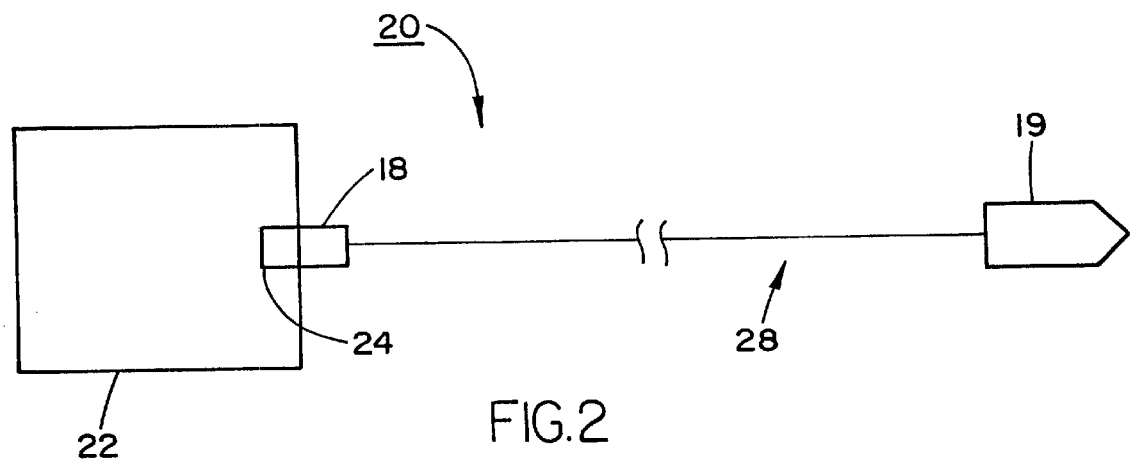
FIG. 2 illustrates a schematic representation of a laser device utilizing the optical fiber pursuant to the present invention.
Figure 3:
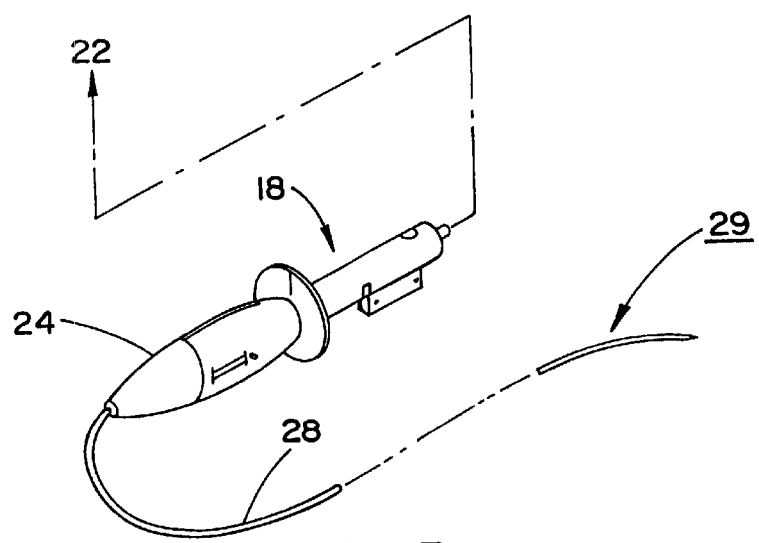
FIG. 3 illustrates a diagrammatic perspective view of an optical fiber assembly incorporating an embodiment of the present invention.

Illustrated schematically in FIG. 2 is a medical instrument 20 for diffusing light from an optical fiber 28. The medical instrument 20 includes a source of light energy 22, preferably a laser; and wherein the optical fiber 28 connects into the source of light energy 22 through the intermediary of a connector 18 which is attached to a connection port 24 leading to a diffuser portion 19 of the optical fiber. A typical connector and connection port of this kind which can be utilized for the medical instrument 20 is described in Evans et al. U.S. Pat. No. 5,802,229, while a typical laser employable for the medical instrument 20 is the Optima laser which will be sold by Ethicon Endo-Surgery in Cincinnati, Ohio. The optical fiber 28 with the attached connector 18 can be provided and sold separately from the source of light 22, as an optical fiber assembly 29, as represented in FIG. 3 of the drawings.

Figure 4:
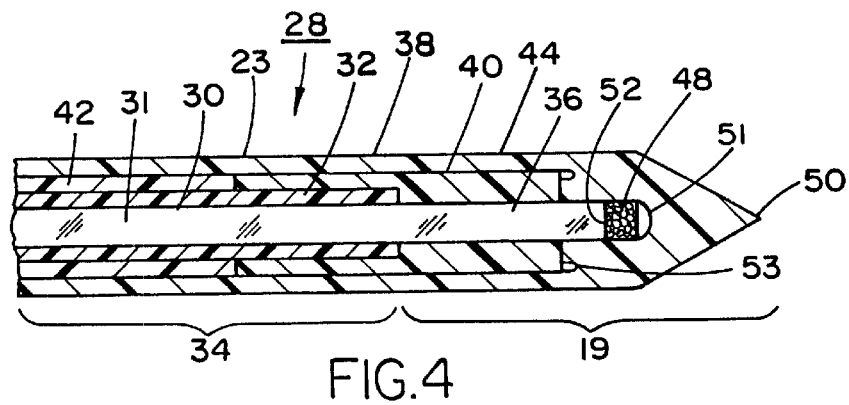
FIG. 4 illustrates a longitudinal sectional view of the inventive optical fiber utilizing a diffuser portion, showing as represented from the interior to the exterior thereof, a core, an optical coupling layer, and an outer sleeve contacting the core distal to the diffuser portion.

A typical optical fiber 28 according to one embodiment of the present invention, including diffuser portion 19 and a proximal light-transmitting portion 34 is shown in FIG. 4. In a light-transmitting portion 23 of the optical fiber 28, a cladding 32 and the proximal portion 34 of a sleeve 38 radially surround the proximal portion 30 of a core 31. The optical fiber 28 may also have a buffer layer 42 arranged to extend circumferentially between the cladding 32 and the sleeve 38. The material used to form the cladding 32 has an index of refraction lower than the index of refraction of the material used to create the core 31 so as to contain the light within the core 31. The core 31, in addition to its proximal portion 30, extends through a distal portion 36 to the distal end 52 thereof. The distal portion 36 of the core 31 which is employed to diffuse light, is surrounded by an optical coupling layer 40 and the distal portion 44 of the sleeve 38. There is no interruption, discontinuity, or weld joint on the sleeve 38 inasmuch as the proximal portion 34 of the sleeve 38 and the distal portion 44 of the sleeve 38 are two segments of one continuous unitarily constructed sleeve 38. The sleeve 38 can extend distally past the distal end 52 of the core 31 and may be configured to penetrating tip 50. The sleeve 38, as mentioned, is constituted of one continuous piece, preferably consisting of perfluoroalkoxy impregnated with barium sulfate.

A material having an index of refraction higher than the index of refraction of the core 31 forms the optical coupling layer 40, wherein UV50 Adhesive, available from Chemence, Incorporated, in Alpharetta, Ga., can be used to produce the optical coupling layer 40.

A light-scattering component 48 which is filled with a light-scattering material and located on the distal face 52 of the core 31 can reflect light back into the core 31 so as to provide a more even or uniform light distribution, whereby alexandrite can be employed as the light-scattering material for component 48. In addition to its light-scattering properties, the material fluoresces in a temperature-dependent manner upon being stimulated by light, with this property adapted to be used to measure temperature in tissue in proximity to the diffuser portion 19. The same adhesive which is employed for the optical coupling layer 40 can suspend the alexandrite particles therein and can serve as the base material for the light-scattering component 48.

Figure 7:
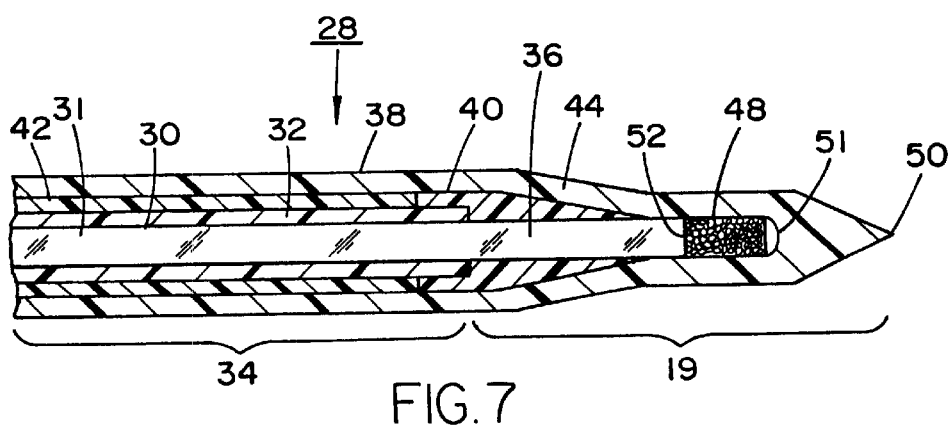
FIG. 7 illustrates a longitudinal sectional view of an embodiment of an optical fiber utilizing the inventive diffuser portion showing, as represented from the interior to the exterior, a core, an optical coupling layer, and an outer sleeve contacting the core distal to the diffuser portion.

As illustrated in, respectively, FIGS. 4 and 7, utilizing the light-scattering component 48, the sleeve 38 is shaped to extend distally past the light-scattering component 48 and resultingly forms a pointed penetrating tip 50.

During operation of the medical instrument 20, light generated by the source of light energy 22 travels through the core 31 to the diffuser portion 19. There, in the embodiment of the invention illustrated in FIG. 4, light energy emerges from the core 31 to the optical coupling layer 40 because of the optical coupling layer having a higher index of refraction. The distal portion 44 of the sleeve 38 which surrounds the optical coupling layer 40, collects the light from the optical layer 40, employing the abrasions formed on the inner surface of the distal portion 44 of the sleeve 38. The sleeve 38 preferably uses barium sulfate particles scattered within the sleeve 38 to direct light energy evenly outwards towards the tissue. Light energy reaching the light-scattering component 48 is reflected back towards the core 31 by the alexandrite particles in the light-scattering component 48. Moreover, the fluorescent properties of the alexandrite particles, when stimulated by light energy of the proper wavelength, can determine the temperature of surrounding tissues employing methods which are known in the art. The penetrating tip 50 is capable of piercing tough tissue in order to assist medical procedures.

The inventive sleeve 38 has no weld joints or discontinuities in the outer diameter extending from the proximal end of the penetrating tip 50 to the connector 18 which conceivably tend to weaken the optical fiber 28, or which may detrimentally catch or drag the optical fiber 28 so as to displace the latter while in use. When using the optical fiber 28, surgeons or medical practitioners often need to bend it to successfully locate the fiber in the body of a patient. The optical fiber 28 and the associated sleeve 38 can withstand more bending than optical fibers with sleeves which have weld lines or discontinuities formed in the outer diameter thereof proximal to the penetrating tip 50.

Method of Forming the Optical Fiber

In order to produce an optical fiber according to the invention as shown in FIG. 4, there can be modified an optical fiber 28 with its associated sleeve 38. First, a sleeve 38 is provided which is approximately as long as the optical fiber to be used, and preferably long enough to extend from the connector 18 (shown in FIG. 3) past the distal face 52 of the core 31. Thereafter, the inner surface of the distal portion 34 of the sleeve 38 is abraded. Different methods can be used to abrade, texture, or roughen the inner surface, such as brushing with a small brush, roughening with a small tool, or pressing against a mandrel to mold in rough areas, can all be employed in order to create a rough inner surface. The roughening process can be implemented while the sleeve 38 is a separate piece before its assembly with the other components of the optical fiber 28, or it can be effected subsequent to assembly. In case the roughening process is performed after assembling the sleeve to the fiber, the sleeve 38 is slid over the buffer layer 42 so as to extend the sleeve 38 distally beyond the distal end of the buffer layer 42 and core 31. Moving the sleeve 38 distally beyond the distal end of the buffer layer 42 and core 31 will expose the interior of the sleeve 38 so that it can be easily abraded.

After abrading, in order to prepare the optical fiber 28 for assembly, the distal portion 36 of the core 31 is exposed by stripping away the buffer layer 42 and the surrounding cladding 32. Leaving the cladding 32 so as to extend distally beyond the end of the buffer layer 42 in a stepped manner, as shown in FIG. 4, reduces the formation of any stress concentration points.

Figure 5:
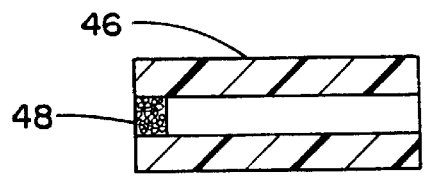
FIG. 5 illustrates a fragmentary sectional view showing the annulus material containing a light-scattering component.

In order to make the light-scattering component 48, a mix of alexandrite particles and uncured adhesive, preferably in a ratio of 2.5 to 1 of alexandrite to adhesive by weight, is conveyed into a tube material used for annulus 46, and having an inner diameter which is equal to the outer diameter of the core 19. The annulus material should be long enough to extend well beyond the end of the sleeve 38 upon assembly. The mix of uncured light-scattering component material is an axial length of annulus material 46 containing the light-scattering component 48, as shown in FIG. 5.

Figure 6:
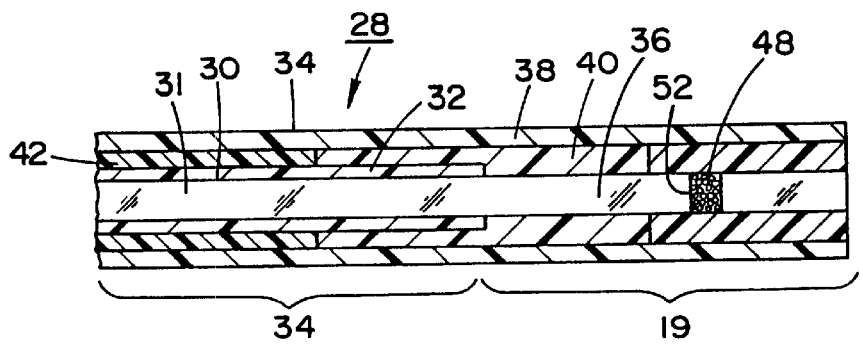
FIG. 6 illustrates a longitudinal sectional view showing the annulus assembled to the core prior to implementing the tipping step in an optical fiber utilizing the inventive diffuser portion.

The sleeve 38 is then slid over the prepared core 31 and buffer layer 42 until the sleeve 38 extends beyond the distal face 52 of the core 31. Uncured adhesive 53 is then applied to the empty volume or space left by the buffer layer 42 and cladding 32 having been previously removed. The sleeve 38 is moved so as to extend the core 31 slightly beyond the end of the sleeve 38, and the length of annulus material containing the uncured light-scattering component material is then fitted over the end of the exposed core 19. The light-scattering component material should abut the distal face 52 of the core 19 and a small length of annulus material should surround the core 19 near its distal face 52. The core 31, the light-scattering component material, and a length of annulus material are then recessed or withdrawn into the sleeve 38, leaving a length of annulus material extending beyond the distal face 52 of the core 31, and substantially the same distance beyond face 52 as sleeve 38, illustrated in FIG. 6. In case no light-scattering component 48 is needed, the length of annulus material without the light-scattering component 48 is positioned around the core 31 near its distal face 52.

In an optional step, there may be removed any air bubbles which may be present in the optical coupling layer 40. The distal end of the optical fiber 28 with the distal face 52 of the core 31 is held down while being heated to allow the adhesive that will form the optical coupling layer 40 to flow towards the distal end under the effect of gravity. This step will assist in eliminating air from the optical coupling layer 40 in order to allow it to transmit light from the core 31 more efficiently, whereby, for instance, heat can be applied with a heat gun.

With the annulus material in place, the adhesive and the light-scattering component material are cured to form the optical coupling layer and light-scattering component 48 whereby pursuant to one embodiment of the invention, the adhesive can be cured by means of ultraviolet light.

The penetrating tip 50 is formed by placing the distal end of the optical fiber into a mold and heating it to melt and fuse the sleeve 38 and the annulus 46 into one piece, producing the embodiment shown in FIG. 4, leaving a small air pocket 51 in conjunction with the light-scattering component 48.

In one embodiment of the invention, both the annulus 46 and the sleeve 38 are made of the same material and formed into one piece so that the annulus 46 becomes a part of the sleeve 38 once the parts are melted and fused. The annulus 46, as a portion of the sleeve 38, contacts the core 31 at the distal portion 36 of the core. It also contacts and aligns the light-scattering component 48 upon use of the light scattering component 48. The penetrating tip 50 being formed on the optical fiber 28, referred to as tipping, completes the diffuser portion 19 on the optical fiber 28.

Another method of forming an embodiment of the optical fiber pursuant to the invention produces the configuration shown in FIG. 7. In order to produce this embodiment, the cladding 32 and the buffer layer 42 are first stripped from the core 31, as described in the previous method. The distal portion 44 of the sleeve 38 is abraded as before. The sleeve 38 is then displaced so as to extend past at least the distal face 52 of the core 31. Using an adhesive which is curable into an optical coupling layer 40, the void left by the removed buffer layer 42 and cladding 32 is then filled. If the light-scattering component 48 is used, the light-scattering component 48 is pushed through the uncured adhesive to the distal face 52 of the core 31. In order to close the end of sleeve 38, the sleeve end is heated in a mold which forces the sleeve 38 radially towards the core 31 to thereby form the embodiment shown in FIG. 7, with the sleeve 38 connecting the core 31 and the light-scattering component 48, and air pocket 51 formed within tip 50. The adhesive is cured into the optical coupling layer 40, whereby in one embodiment of the invention, ultraviolet light can be used to cure the adhesive.

It is readily apparent that equivalent structures may be substituted for the structures illustrated and described herein and that the described embodiments of the invention are not limited to those elucidated. As one example of an equivalent structure which may be used, the optical coupling layer 28 can comprise a substance filled with light-scattering particles, which if employed eliminates need to abrade the inner surface of the sleeve 38.

While the invention has been particularly shown and described with respect to preferred embodiments thereof, it will be understood by those skilled in the art that the foregoing and other changes in form and details may be made therein without departing form the spirit and scope of the invention.

What is claimed is:

1. A medical instrument for the treatment of tissue, said medical instrument including a source of light energy; and a connector removably attachable to said source of light energy; and an optical fiber having a proximal end, connected to said connector, and a distal end positionable at a site of the treatment, said optical fiber comprising:
- a core having a distal portion and a distal face proximate said distal end of the optical fiber;
- an optical coupling layer radially surrounding said distal portion of said core; and
- a sleeve of unitary construction radially surrounding said optical coupling layer extending continuously and uninterrupted along the length of said optical fiber from said distal face of said core to said connector, and wherein said sleeve contacts said core at said distal portion.

2. The medical instrument according to claim 1, wherein said sleeve forms a penetrating tip distal to said distal face of said core.

3. The medical instrument according to claim 2, wherein said optical fiber further comprises a light-scattering component affixed to said distal face of said core.

4. A method of producing a medical instrument for the treatment of tissue, said instruments including an optical fiber having a core, a cladding and a continuous uninterrupted sleeve; said method comprising:
  a) stripping said cladding from said optical fiber so as to leave a volume between the core of said optical fiber and the sleeve of said optical fiber;
  b) filling said volume with a material curable into an optical coupling layer; and
  c) molding a penetrating tip at a distal end of said optical fiber, while causing said sleeve to touch said core.

5. The method according to claim 4, wherein said core includes a distal end, said method further comprising placing a light-scattering component at said distal end of said core.

6. A method according to claim 4, wherein said core has a distal portion, further comprising:
  d) placing an annulus over said distal portion of said core;
  e) filling said volume with a material curable into an optical coupling layer; and
  f) molding a penetrating tip at a distal end of said optical fiber while fusing said annulus to said sleeve to cause said sleeve to touch said core.

7. The method according to claim 6, further comprising forming a light-scattering component inside said annulus.

8. The method according to claim 4, wherein said sleeve is radially compressed to cause said sleeve to touch said cove while molding said penetrating tip.

9. An optical fiber assembly having a proximal end and a distal end, said optical fiber assembly comprising:
  a) a core having a distal portion and a distal face;
  b) an optical coupling layer radially surrounding said distal end of the optical fiber assembly core;
  c) a connector affixed at said proximal end of said optical fiber assembly; and
  d) a sleeve radially surrounding said optical coupling layer and extending continuously and uninterruptedly from said distal face of said core to said connector, and wherein said sleeve contacts said core at said distal portion.

10. The optical fiber assembly according to claim 9, wherein said sleeve forms a penetrating tip distal to the distal face to said core.

11. The optical fiber assembly according to claim 10, comprising a light-scattering component affixed to said distal face of said core.

12. The optical fiber assembly according to claim 9, wherein said sleeve is of a unitary, single-piece construction.

* * * * *